United States Patent [19]
Webler et al.

[11] Patent Number: 5,330,444
[45] Date of Patent: Jul. 19, 1994

[54] CATHETER TIP WITH A LOW FRICTION LINING AND METHOD OF USE

[75] Inventors: William E. Webler, Costa Mesa; Viet P. Dinh, Santa Ana, both of Calif.

[73] Assignee: Intertherapy, Inc., Santa Ana, Calif.

[21] Appl. No.: 945,175

[22] Filed: Sep. 15, 1992

[51] Int. Cl.⁵ ............................... A61M 5/32
[52] U.S. Cl. ............................ 604/265; 604/280
[58] Field of Search ................. 128/656–658; 604/96, 102, 53, 264, 265, 280, 282; 606/192, 194

[56] References Cited

U.S. PATENT DOCUMENTS

| 4,748,982 | 6/1988 | Horzewski et al. | 604/102 X |
| 4,771,777 | 9/1988 | Horzewski et al. | 604/101 X |
| 4,824,435 | 4/1989 | Giesy | 604/49 |
| 4,951,677 | 8/1990 | Crowley | 128/662.064 |
| 5,024,234 | 6/1991 | Leary | 128/663.81 |
| 5,034,001 | 7/1991 | Garrison et al. | 604/53 |
| 5,047,045 | 9/1991 | Arney et al. | 606/194 |
| 5,100,381 | 3/1992 | Burns | 604/96 |
| 5,135,535 | 8/1992 | Kramer | 606/194 |
| 5,156,594 | 10/1992 | Keith | 604/96 |
| 5,176,698 | 1/1993 | Burns et al. | 606/192 |
| 5,180,367 | 1/1993 | Kontos et al. | 604/101 |

OTHER PUBLICATIONS

Boston Scientific Advertising Flyer (one-page, undated).

Primary Examiner—C. Fred Rosenbaum
Assistant Examiner—Corrine Maglione
Attorney, Agent, or Firm—Lyon & Lyon

[57] ABSTRACT

A monorail tip catheter includes a low friction guide wire lumen to facilitate removal of the catheter over the guide wire without buckling or kinking the guide wire. The catheter guide wire lumen is provided with a low friction lining with anchoring means, together with additional guide means to facilitate threading the guide wire into the monorail guide wire lumen.

18 Claims, 3 Drawing Sheets

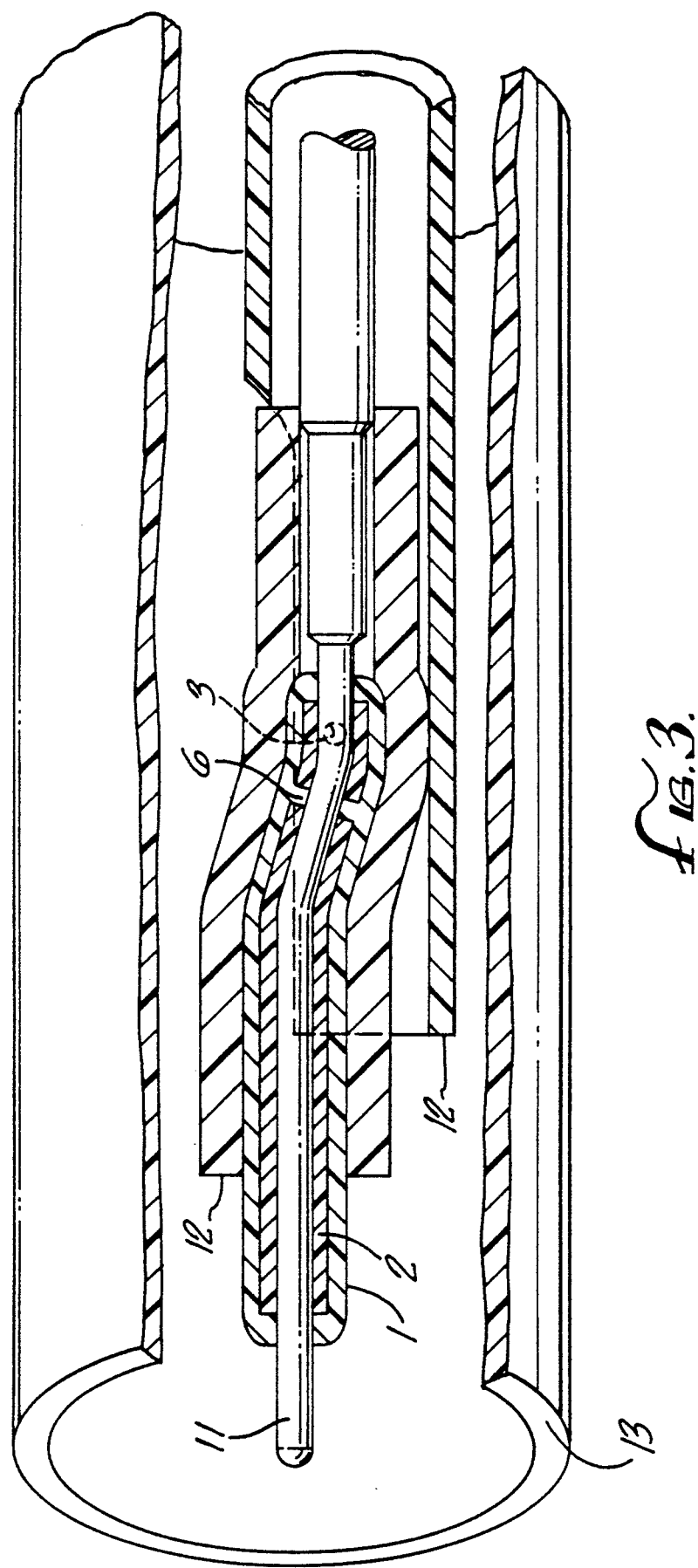

CATHETER TIP WITH A LOW FRICTION LINING AND METHOD OF USE

FIELD OF THE INVENTION

This invention relates to the field of intravascular catheters. Specifically, the invention is directed towards improvements in monorail catheter tip construction.

BACKGROUND OF THE INVENTION

Intravascular catheters and probes are used for a variety of diagnoses and treatments of vascular diseases and defects. Similar catheters are also used for examination and treatment of other body cavities and vessels. These catheters are inserted in the body until they reach the location of interest. In the case of intravascular catheters used for diagnoses of the coronary arteries, the catheter is inserted in the femoral artery and guided up through the descending aorta, arch of the aorta, down the ascending aorta, then into the left or right coronary arteries, continuing as far into the coronary arteries as the miniaturization of the catheter will allow. The small diameter of the vessels and the delicacy of the vessels necessitate great care in catheter deployment and removal, in order to avoid damage to the vessels. The delicacy and small size of the vessels, combined with the tortuous deployment path, impose severe restrictions on materials and structures used for such intravascular catheters.

One method of deploying intravascular catheters is called the monorail system. In the monorail system, a small diameter guide wire is first routed along the deployment path. When the guide wire is properly positioned, its distal tip lies in the coronary artery, just past the area of interest, and the proximal end extends out of the patient's thigh. Standard introducers and guide catheters may be used in the procedure.

When the guide wire is properly positioned, the proximal end of the guide wire is threaded through the monorail lumen of the diagnostic catheter. In a monorail tip catheter, the tip of the catheter is provided with a small lumen to receive the guide wire. The lumen starts at the extreme distal tip of the catheter, runs a short length from the distal tip before reaching the catheter circumference to provide an exit port very close to the distal tip. The guide wire is threaded through this lumen. Thus mounted, the diagnostic catheter is pushed into the femoral artery along the entire deployment path and further into the coronary artery, guided to the diagnostic site by the guide wire. In this manner, the guide wire facilitates placement of the diagnostic catheter.

The diagnostic catheter may identify sites for treatment such as atherectomy. The diagnostic catheter can be pulled out of the body while the guide wire remains in place so that a working catheter can be deployed along the same guide wire to the treatment site. The use of a stationary guide wire facilitates deployment of the working catheter to the treatment site previously identified by the diagnostic catheter. In some instances, the diagnostic and working mechanisms can be deployed on a single catheter, avoiding the need to use them sequentially.

A problem sometimes encountered with the monorail tip catheter is that, during withdrawal of the catheter over the guide wire, friction between the monorail lumen and the guide wire makes it difficult to withdraw the catheter without buckling the guide wire. Frictional and buckling forces are exacerbated by the tortuous bends which the catheter must negotiate during withdrawal, combined with the low rigidity of the guide wire. During withdrawal, the monorail tip is effectively axially pushing on the portion of the guide wire proximal to the monorail lumen. This may cause binding, applying excessive force on the guide wire, which force may cause damage to the arteries. Worse yet, the binding may cause the guide wire to become kinked so that withdrawal of the catheter over the guide wire is not possible, and withdrawal of the kinked guide wire is likely to damage the vessel's internal surface along the withdrawal path.

SUMMARY OF THE INVENTION

It is a principal object of the invention to eliminate or minimize friction between the guide wire lumen of a catheter and the guide wire. It is also an object of the invention to provide a low friction surface for the monorail lumen.

These and other useful objects are achieved by the present invention which is an improved catheter tip especially suited for low friction coupling to a guide wire. The present invention includes a catheter tip with a low friction resin lining for the monorail, along with suitable structures for securely mounting the lining in the monorail lumen.

BRIEF DESCRIPTION OF THE DRAWINGS

FIG. 3 is a longitudinal cross-sectional view of the monorail lumen with a low friction lining and tapered tip.

DETAILED DESCRIPTION OF THE INVENTION

Figure 1:
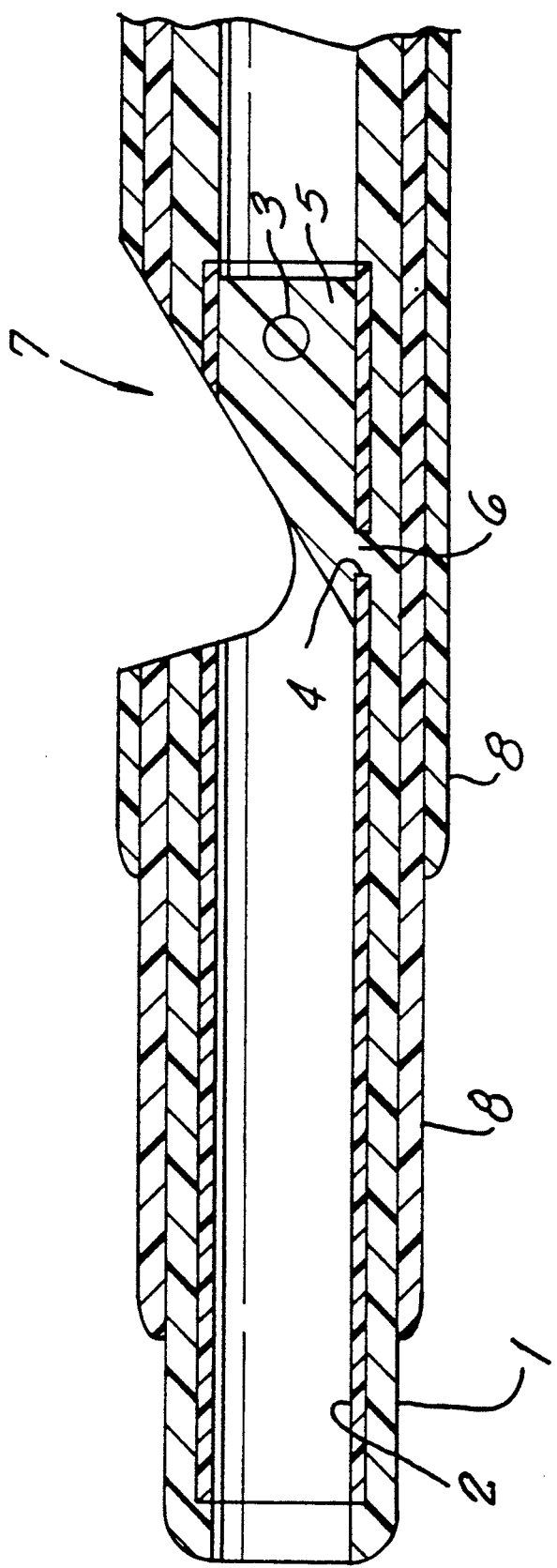
FIG. 1 is a longitudinal cross-section of the monorail lumen with a low friction lining.

FIG. 1 shows an embodiment of the monorail catheter with a low friction insert. The catheter tip 1 is of a small internal diameter and is made of polyethylene, ethyl vinyl acetate or other suitable material. The low friction tube 2 is held within the catheter tip 1. The proximal end of the low friction tube 2 is provided with one pair of opposing anchoring holes, one of which is shown as anchoring hole 3. Just distal of the anchoring holes, the low friction tube 2 is provided with another wedge anchoring hole 4. Inside the low friction tube 2 is a plug 5. The plug 5 has a wedge shape at its distal end and the wedge is provided with a concave surface to assist in guiding the wire guide. Anchoring pins 6 fix the plug 5 to the catheter tip 1. An exit port 7 allows a guide wire inserted in the distal opening of the low friction lumen to pass out of the low friction lumen. The wedge of the plug 5 helps guide the guide wire out of the lumen and prevent snagging as the lumen is threaded. At the very tip of the assembly, the internal diameter of the catheter tip 1 is the same as the internal diameter of the low friction tube 2. This provides an additional anchoring structure, and also provides a smooth bore which facilitates threading the guide wire through the low friction lumen.

Figure 2:
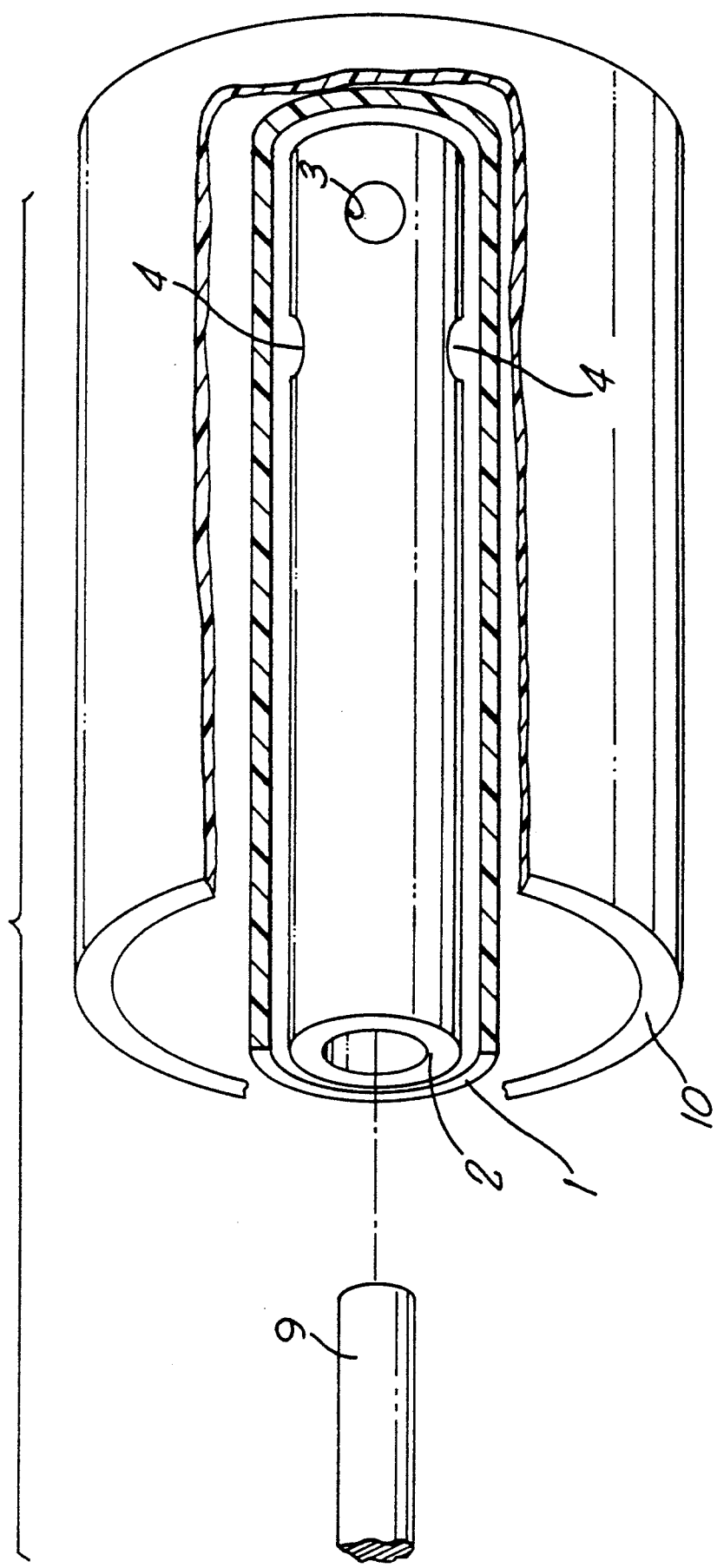
FIG. 2 is a longitudinal cross-section of the monorail lumen with a low friction lining together with accessory parts used in its fabrication.

The assembly may be formed as shown in FIG. 2. A low friction tube 2 is provided with two pairs of holes at its proximal end, each pair offset by 90°. The proximal pair of holes will correspond to the anchoring holes 3 of FIG. 1 and the distal holes will correspond to the wedge anchoring hole 4 of FIG. 1, as will become apparent in later steps of the process. The low friction tube is placed on a straight mandrel 8 of matching diameter. The straight mandrel 8 is inserted along the entire length of the low friction tube 2. The low friction tube 2 is covered with the catheter tip 1, and this assembly is covered with a plastic compression tube 9 made of Silastic ® plastic or other suitable material. The Silastic ® plastic, when soaked with a solvent, expands to a large diameter so that it may be easily slipped over the catheter assembly. The Silastic ® plastic compression tube 9 shrinks when the solvent evaporates, exerting considerable force on the catheter assembly. This assembly is heated so that the catheter tip 1 melts to fill the anchoring holes 3 and wedge anchoring holes 4 thereby forming anchoring pins which will secure the low friction tube 2. At the distal tip of the assembly, the catheter tip 1 melts to conform to the mandrel, forming a flange which also helps to secure the low friction tube 2. The low friction tube 2 can be etched to enhance adherence between the low friction tube 2 and the catheter tip 1. A gold ring can be secured at the distal tip of this assembly to provide a radiopaque marker.

FIG. 3 shows another embodiment in which the low friction tube 2 is disposed within a catheter tip 1 which is tapered. The angle of the axis of the guide wire lumen in relation to the axis of the tapered tip allows for the guide wire to pass through a relatively straight guide wire lumen. As shown in FIG. 3, the proximal end of the low friction tube 2 can be bent toward the axis of the catheter tip 1 so that plug 5 may be used to secure the low friction tube 2 in place without enlarging the diameter of the proximal portion of the catheter tip 1.

The inventors have found that Teflon ® fluorinated resins or polytetrafluoroethylene are suitable for the low friction tube, ethyl vinyl acetate is suitable for the plug and tip, and polyethylene is suitable for the tip.

While the preferred embodiment of the invention has been described, it is merely illustrative of the principles of the invention. Other embodiments and configurations may be devised without departing from the spirit of the invention and the scope of the appended claims. Specifically, it is expected that new materials will be developed which may prove suitable for the uses described in the preferred embodiment.

We claim:

1. A catheter with a distal end, distal tip, and proximal end comprising a short lumen at its distal end, said short lumen extending from the distal end of the catheter a small proximal distance from the distal end, said short lumen terminating at its proximal end at the side of the catheter; an exit port at the proximal end of the short lumen communicating with said short lumen, and a low friction tube secured to the internal wall of the short lumen by means of an anchoring system comprising a plug made of a material which is bondable to the catheter, and at least one anchoring hole in the proximal end of the low friction tube through which the anchor plug is bonded to the catheter material thereby locking the low friction tube in place.

2. The catheter of claim 1 wherein the axis of the lumen is offset from the axis of the distal tip, so that the lumen extends from the center of the distal tip of the lumen to an exit port located on the circumference of the distal tip.

3. The catheter of claim 1 further comprising a wedge shaped distal portion on the plug, said wedge shaped distal portion disposed beneath the exit port.

4. The catheter of claim 1 further comprising a distal flange on the distal tip of the catheter, the internal diameter of said distal flange matching the internal diameter of the low friction tube, said distal flange being integrally formed with short lumen.

5. The catheter of claim 3 wherein the anchoring hole is disposed beneath the wedge shaped distal portion of the plug.

6. The catheter of claim 1 further comprising at least one additional anchoring hole communicating between the catheter material and the plug, through which the catheter material and plug are joined.

7. A catheter with a distal end, distal tip, and proximal end comprising a short lumen at its distal end, said short lumen extending from the distal tip of the catheter a small proximal distance from the distal tip, said short lumen terminating at its proximal end at the side of the catheter; an exit port at the proximal end of the short lumen communicating with said short lumen, and a low friction tube secured to the internal wall of the short lumen by means of an anchoring system comprising a plug made of a material which is bondable to the catheter, and at least one anchoring hole in the proximal end of the low friction tube through which the anchor plug is bonded to the catheter material thereby locking the low friction tube in place, and a distal flange on the distal tip of the catheter, the internal diameter of said distal flange matching the internal diameter of the low friction tube, said distal flange being integrally formed with the short lumen.

8. A catheter with a distal end, distal tip, and proximal end comprising a short lumen at its distal end, said short lumen extending from the distal end of the catheter a small proximal distance from the distal end, said short lumen terminating at its proximal end at the side of the catheter; an exit port at the proximal end of the short lumen communicating with said short lumen, and a low friction lining secured to the internal wall of the short lumen by means of an anchoring system comprising a plug made of a material which is bondable to the catheter, a wedge shaped distal portion on the plug, said wedge shaped distal portion disposed beneath the exit port, and at least one anchoring hole in the proximal end of the low friction lining through which the anchor plug is bonded to the catheter material thereby locking the low friction tube in place, at least one of said anchoring holes disposed beneath the wedge shaped distal portion of the plug.

9. A catheter with a distal end, distal tip, and proximal end comprising a short lumen at its distal end, said short lumen extending from the distal tip of the catheter a small proximal distance from the distal tip, said short lumen terminating at its proximal end at the side of the catheter; an exit port at the proximal end of the short lumen communicating with said short lumen, and a low friction tube secured to the internal wall of the short lumen by means of an anchoring system comprising a plug made of a material which is bondable to the catheter, and at least one anchoring hole in the proximal end of the low friction tube through which the anchor plug is bonded to the catheter material thereby locking the low friction tube in place, and at least one additional anchoring hole communicating between the catheter material and the plug, through which the catheter material and plug are joined.

10. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of the tapered catheter tip;

a plug disposed within the proximal end of the low friction tube, said plug being joined to the tapered catheter tip through the anchor holes and wedge anchoring hole;

said plug further comprising a wedge shaped distal portion;

said lumen of the tapered catheter tip with its distal axis offset from the axis of the tapered catheter tip, so that the low friction tube extends proximally from the distal extremity of the catheter tip, along the tapered side; and an exit port on the side of the tapered catheter tip, located near the proximal end of the low friction tube and communicating therewith.

11. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of the tapered catheter tip;

said tapered catheter tip extending distally of the distal end of the low friction tube, and the extending portion of the tapered catheter tip being of the same internal diameter as the low friction tube;

a plug disposed within the proximal end of the low friction tube, said plug being joined to the tapered catheter tip through the anchor holes and wedge anchoring hole;

said plug further comprising a wedge shaped distal portion;

said lumen of the tapered catheter tip with its distal axis offset from the axis of the tapered catheter tip, so that the low friction tube extends proximally from the distal extremity of the catheter tip, along the tapered side; and an exit port on the side of the tapered catheter tip, located near the proximal end of the low friction tube and communicating therewith.

12. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of tapered catheter tip;

said tapered catheter tip extending distally of the distal end of the low friction tube, and the extending portion of the tapered catheter tip being of the same internal diameter as the low friction tube;

a plug disposed within the proximal end of the low friction tube, said plug being joined to the tapered catheter tip through the anchor holes and wedge anchoring hole;

said plug further comprising a wedge shaped distal portion, said wedge shaped distal portion having a concave distal surface;

said lumen of the tapered catheter tip with its distal axis offset from the axis of the tapered catheter tip, so that the low friction tube extends proximally from the distal extremity of the tapered catheter tip, along the tapered side; and an exit port on the side of the tapered catheter tip, located near the proximal end of the low friction tube and communicating therewith.

13. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of the tapered catheter tip;

said low friction tube forming a lumen which is generally straight at its distal end and bent at its proximal end;

plug disposed within the proximal end of the low friction tube, said plug being joined to the tapered catheter tip through the anchor holes and wedge anchoring hole;

said plug further comprising a wedge shaped distal portion;

said low friction tube positioned within the tapered catheter tip with its distal axis offset from the axis of the tapered catheter tip, so that the straight distal portion of the low friction tube extends from the distal extremity of the catheter tip, along the tapered side, and the bend of the low friction lumen turns inward toward the axis of the tapered catheter tip; and an exit port on the side of the tapered catheter tip, located in the vicinity of the bend of the low friction tube and the wedge shaped distal portion of the plug.

14. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of the tapered catheter tip;

said tapered catheter tip extending distally of the distal end of the low friction tube, and the extending portion of the tapered catheter tip being of the same internal diameter as the low friction tube;

said low friction tube forming a lumen which is generally straight at its distal end and bent at its proximal end;

plug disposed within the proximal end of the low friction tube, said plug being joined to the tapered catheter tip through the anchor holes and wedge anchoring hole;

said plug further comprising a wedge shaped distal portion;

said low friction tube positioned within the tapered catheter tip with its distal axis offset from the axis of the tapered catheter tip, so that the straight distal portion of the low friction tube extends from the distal extremity of the catheter tip, along the tapered side, and the bend of the low friction lumen turns inward toward the axis of the tapered catheter tip; and an exit port on the side of the tapered catheter tip, located in the vicinity of the bend of the low friction tube and the wedge shaped distal portion of the plug.

15. A monorail catheter tip comprising:

a tapered catheter tip having a lumen therein;

a low friction tube with at least one anchoring hole at its proximal end, and at least one wedge anchoring hole just distal of the anchor holes, said low friction tube being disposed within the lumen of the tapered catheter tip;

said tapered catheter tip extending distally of the distal end of the low friction tube, and the extending portion of the tapered catheter tip being of the same internal diameter as the low friction tube;

said low friction tube forming a lumen which is generally straight at its distal end and bent at its proximal end;

a plug disposed within the proximal end of the low friction tube, said plug being joined to the tapered catheter tip through the anchor holes and wedge anchoring hole;

said plug further comprising a wedge shaped distal portion, said wedge shaped distal portion having a concave distal surface;

said low friction tube positioned within the tapered catheter tip with its distal axis offset from the axis of the tapered catheter tip, so that the straight distal portion of the low friction tube extends from the distal extremity of the tapered catheter tip, along the tapered side, and the bend of the low friction lumen turns inward toward the axis of the tapered catheter tip; and an exit port on the side of the tapered catheter tip, located in the vicinity of the bend of the low friction tube and the wedge shaped distal portion of the plug.

16. A catheter tube with a low friction lining comprising:

a catheter tube with a lumen defined by an inner diameter;

a low friction tube with at least one anchoring hole at its proximal end, and at least one wedge anchoring hole just distal of the anchor holes, said low friction tube being disposed within the lumen of the catheter tube, said low friction tube having an outer diameter matching the inner diameter of the catheter tube;

a plug disposed within the proximal end of the low friction tube, said plug being joined to the catheter tube through the anchor holes and wedge anchoring hole;

said plug further comprising a wedge shaped distal portion; and an exit port on the side of the catheter tube near the wedge shaped distal portion of the plug.

17. A method of inserting a catheter along a deployment path within the body, said method comprising the steps of:

providing a catheter with a distal end, distal tip, and proximal end comprising a short lumen at its distal end, said short lumen extending from the distal end of the catheter a small proximal distance from the distal end, said short lumen terminating at its proximal end at the side of the catheter; an exit port at the proximal end of the short lumen communicating with said short lumen, and a low friction tube secured to the internal wall of the short lumen by means of an anchoring system comprising a plug made of a material which is bondable to the catheter, and at least one anchoring hole in the proximal end of the low friction tube through which the anchor plug is bonded to the catheter material thereby locking the low friction tube in place;

placing a guide wire along the deployment path so that its distal end extends just past the area within the body to be examined or treated by the catheter;

threading the proximal end of the guide wire into the distal end of the short lumen and out the exit port of the short lumen;

pushing the threaded distal tip of the catheter along the guide wire to the area within the body to be examined or treated by the catheter.

18. The method of claim 17 further comprising the steps of withdrawing the catheter while leaving the guidewire in place.

* * * * *